US008553898B2

(12) United States Patent
Raftery

(10) Patent No.: US 8,553,898 B2
(45) Date of Patent: Oct. 8, 2013

(54) METHOD AND SYSTEM FOR REDUCING ACOUSTICAL REVERBERATIONS IN AN AT LEAST PARTIALLY ENCLOSED SPACE

(76) Inventor: Emmet Raftery, Ontario (CA)

( * ) Notice: Subject to any disclaimer, the term of this patent is extended or adjusted under 35 U.S.C. 154(b) by 954 days.

(21) Appl. No.: 12/627,608

(22) Filed: Nov. 30, 2009

(65) Prior Publication Data

US 2011/0129096 A1 Jun. 2, 2011

(51) Int. Cl.

| | |
|---|---|
| ***H04B 3/20*** | (2006.01) |
| ***A61F 11/06*** | (2006.01) |
| ***G10K 11/16*** | (2006.01) |
| ***H03B 29/00*** | (2006.01) |

(52) U.S. Cl.
USPC ........... 381/66; 381/71.1; 381/71.2; 381/71.7

(58) Field of Classification Search
USPC ........................ 381/66, 71.1, 71.2, 71.5, 71.7
See application file for complete search history.

(56) References Cited

U.S. PATENT DOCUMENTS

| | | | | |
|---|---|---|---|---|
| 4,677,676 | A * | 6/1987 | Eriksson | 381/71.11 |
| 4,829,590 | A | 5/1989 | Ghose | |
| 4,899,387 | A | 2/1990 | Pass | |
| 5,140,640 | A | 8/1992 | Graupe et al. | |
| 5,216,721 | A * | 6/1993 | Melton | 381/71.11 |
| 5,224,168 | A | 6/1993 | Martinez et al. | |
| 5,363,451 | A | 11/1994 | Martinez | |
| 5,440,641 | A | 8/1995 | Kuusama | |
| 5,524,057 | A | 6/1996 | Akiho et al. | |
| 5,559,891 | A | 9/1996 | Kuusama et al. | |
| 5,699,437 | A | 12/1997 | Finn | |
| 5,834,647 | A | 11/1998 | Gaudriot et al. | |
| 5,889,869 | A | 3/1999 | Botros et al. | |
| 6,654,467 | B1 | 11/2003 | York | |
| 6,795,557 | B1 | 9/2004 | Makivirta et al. | |

FOREIGN PATENT DOCUMENTS

| | | | |
|---|---|---|---|
| CA | 2011674 | | 3/1989 |
| CA | 2322809 | A1 | 9/1999 |
| EP | 0555787 | A2 | 8/1993 |
| EP | 0746134 | A2 | 12/1996 |
| WO | WO 97/08683 | | 8/1995 |

OTHER PUBLICATIONS

Arthur Noxon, “Auditorium Acoustics 104”, Sep. 2002, http://www.church-acoustics.com/pdf/aa104.pdf.
PCT/CA2010/001868 International Search Report Mar. 2, 2011.

* cited by examiner

*Primary Examiner* — Vivian Chin
*Assistant Examiner* — Douglas Suthers
(74) *Attorney, Agent, or Firm* — Millman IP Inc.

(57) ABSTRACT

A method of increasing the intelligibility of an audio broadcast in an at least partially enclosed space from at least one amplified audio source. An input microphone receives an incident audio wavefront at a first position in the at least partially enclosed space. An active noise control system is employed to generate a cancelling audio wavefront having a magnitude substantially equal to the magnitude of incident audio wavefront and a phase substantially opposite to the phase of the incident audio wavefront. The cancelling audio wavefront is broadcast at a second position in the at least partially enclosed space adjacent to a reflective surface of the at least partially enclosed space so as to attenuate the incident audio wavefront substantially at or near the reflective surface in order to reduce reverberations of the incident audio wavefront. In this manner, reverberations which could reduce the intelligibility of the audio broadcast to an audience is reduced.

15 Claims, 5 Drawing Sheets

METHOD AND SYSTEM FOR REDUCING ACOUSTICAL REVERBERATIONS IN AN AT LEAST PARTIALLY ENCLOSED SPACE

FIELD OF THE INVENTION

The invention relates generally to the art of active noise cancellation, and more particularly to a method and system of reducing acoustical reverberations in an at least partially enclosed space.

BACKGROUND OF THE INVENTION

In a public venue such as a large auditorium, excessive reverberation negatively impacts the sound quality of audio material being delivered to an audience. Reverberation is the persistence of sound in a particular space after the original sound dissipates. A reverberation, or reverb, is created when a sound is produced in an enclosed space causing a large number of echoes to build up and then slowly decay as the sound is absorbed by the walls and air. If the ratio of source audio to reverberation is low enough, the source material is masked by the presence of the reflected/reverberant audio. This leads to degradation in the quality of the presented source material, leading to difficulty in understanding speech. If the reverberation time is too long, the presented material sounds 'muddy'. These problems are exacerbated in larger auditoriums, since the larger the auditorium, the longer the delay and the greater the reverberation time.

Ideally, an auditorium should be designed for good acoustics. The shape of the auditorium is a major factor in the ratio of direct to reflected sound arriving at the audience. Sound absorbing material on the walls and ceilings can reduce the amount of sound reflected around an auditorium. Diffuse reflectors placed around the ceilings and walls help prevent the reflections from being too coherent, so that an 'echo' is not perceived.

However, relatively few public venues are actually designed for 'good' acoustics. Music concerts and other public events are usually held in the largest venue possible such as sports arenas because the performer typically wishes to sell as many tickets, and fill as many seats, as possible. However, in these large venues there is typically a severe degradation of the perceived audio due to the delayed reflections and reverberations of the source audio from the walls and ceilings.

One of the simplest techniques of reducing the effects of auditorium reverberation is to elevate the loudspeakers and point the sound in the direction of the audience, and away from the ceiling of the auditorium. This reduces the amount of sound pointed directly at a reflective ceiling and back wall, reducing reflection and hence, reverberation, from these surfaces.

However, this is not always possible, especially in the case of a large venue. Further, if the sound source is perceptively disjointed with the source (singer, speaker, etc . . . ), this can have a negative impact on the audience.

Advancements in electronics have lead to the development of phased array loudspeakers, wherein the timing of sounds arriving at the various loudspeakers in the array allow the source audio to be 'steered' towards the audience.

Another approach is to place loudspeakers throughout the auditorium, pointed at the audience. The human acoustic perception of the source of sound is maintained by delaying the sound at remote loudspeakers so that it arrives at the audience within milliseconds after the sound from the stage.

However, these solutions are not always practical, given the shape and size of a particular venue.

Another approach is based on active sound cancellation, in which a particular sound or noise is monitored and a phase-shifted sound is generated to cancel or reduce the unwanted sound or noise.

For example, U.S. Pat. No. 5,363,451 describes a system and method for cancelling noise in an open space from a particular noise source such as a 'machine'. The system detects noise at the noise source and cancels it at another point.

U.S. Pat. No. 5,699,437 describes a system that employs arrays of microphones to pick up 'noise' emanating from some point inside an auditorium and plays the 'opposite sound' or 'cancelling noise' from loudspeakers situated around the auditorium such that the noise is cancelled at some optimal location in the auditorium (the audience). Note that this solution can improve the sound at a 'sweet spot' in the auditorium, but it can also result in detrimental performance in another area of the same auditorium. Further, this system needs tuning by an expert on installation.

U.S. Pat. No. 6,795,557 describes a method for reducing the level of acoustical reflections in a room by attempting to cancel reflected signals as they go into the intended 'quiet area'. However, at this point it becomes difficult to distinguish between reverberations and source audio, particularly where the room or venue has multiple reflective surfaces where the reverberations are not coherent.

SUMMARY OF THE INVENTION

Generally speaking, the invention attenuates sound at or near a reflection surface in the room in order to prevent or at least reduce the sound from reflecting back into a listening area. The invention thus differs from the prior art where no attempt is made to stop reflections and a 'quiet zone' is created by attenuating sounds that do reflect into the listening area.

According to one aspect of the invention a method is provided for increasing the intelligibility of an audio broadcast in a room from at least one amplified audio source. The method includes: receiving an incident audio wavefront from the amplified audio source at a first position in the room; generating a cancelling audio wavefront having a magnitude substantially equal to the magnitude of incident audio wavefront and a phase substantially opposite to the phase of the incident audio wavefront; and broadcasting the cancelling audio wavefront at a second position in the room, the second position being adjacent to a reflective surface of the room and downstream of the first position relative to the audio source. Thus, the incident audio wavefront is attenuated substantially at or near the reflective surface in order to reduce reflections of the incident audio wavefront.

The incident audio wavefront can be received via at least one input microphone. The cancelling audio wavefront can be broadcast through at least one directional loudspeaker positioned adjacent to, and facing, the reflective surface.

The cancelling loudspeaker is preferably spaced at a distance D away from the input microphone, where D corresponds to the delay time required to generate the cancelling audio wavefront.

To achieve broad coverage, an array of input microphones and corresponding cancelling loudspeakers can be deployed across the breadth of the reflective surface. The array can involve a plurality of independent single-channel sound dampening units, or the components can be interlinked via a multiple-channel active sound control module.

According to another aspect of the invention another method of increasing the intelligibility of an audio broadcast in a room from at least one amplified audio source includes the steps of: deploying at least one input microphone in the room to convert at least one incident audio wavefront into at least one corresponding reference electrical signal; deploying at least one cancelling loudspeaker adjacent a reflective surface in the room to broadcast at least one secondary audio wavefront; deploying at least one error microphone substantially at the reflective surface to convert a superposition of the at least one incident audio wavefront and the at least one secondary audio wavefront into at least one error electrical signal; generating at least one cancellation signal based on the at least one reference electrical signal so as to minimize the power of the at least one error electrical signal; and converting the cancellation signal into said at least one second audio wavefront.

In the application of this method, each cancelling loudspeaker can be positioned adjacent to the reflective surface and may have a highly directional output directed downstream of the incident audio source. Each cancelling loudspeaker is preferably also spaced at least a distance D away from a corresponding input microphone, where D corresponds to the delay time required to generate the cancelling audio wavefront after the incident audio wavefront is picked up by the input microphone.

For broad coverage, an array of input microphones, an array of cancelling loudspeakers, and an array of error microphones can be deployed across the breadth of one or more reflective surfaces in the room.

In one embodiment, the number of input microphones, cancelling loudspeakers and error microphones can be equal, and each input microphone, cancelling speaker and error microphone triplet form an independent, single-channel, sound dampening unit, with a plurality of single-channel sound dampening units being deployed across the breadth of the reflective surface(s).

In another embodiment the input microphones, cancelling loudspeakers and error microphones can be interlinked via a multiple-channel active sound control module.

BRIEF DESCRIPTION OF THE DRAWINGS

The foregoing and other aspects of the invention will be more readily appreciated having reference to the drawings, wherein.

DETAILED DESCRIPTION OF PREFERRED EMBODIMENTS

Figure 1:
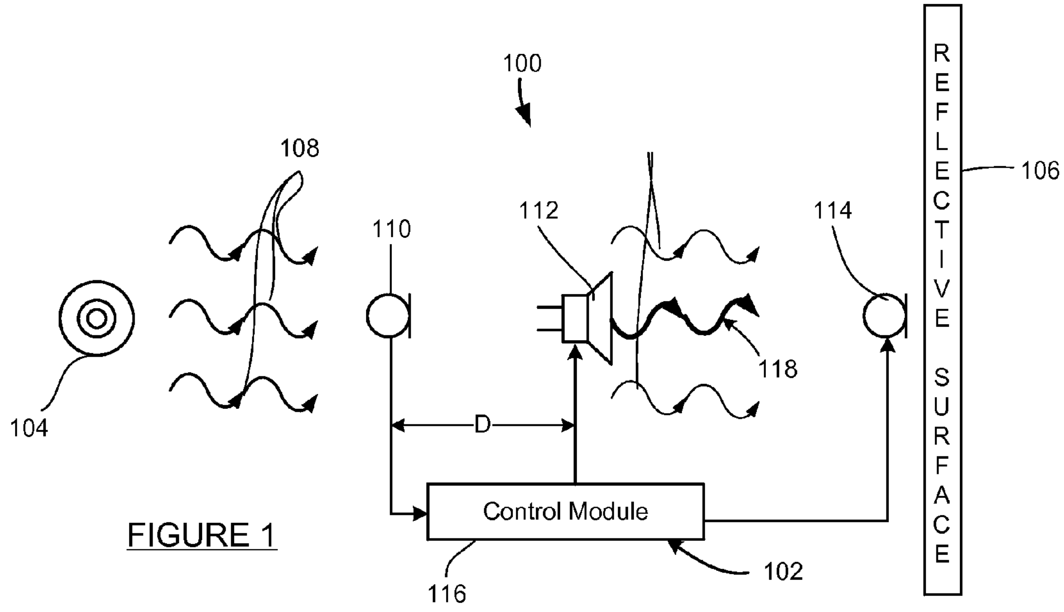
FIG. 1 is a schematic diagram of a reverberation control system according to a first embodiment.

FIG. 1 shows a reverberation control system 100 comprising one sound dampening unit 102. The unit 102 includes an input microphone 110, a noise cancellation loudspeaker 112, and an error microphone 114, all connected to a digital control module 116.

Importantly, the sound dampening unit 102 is installed between an audio source 104 and an acoustic reflective surface 106 such as the rear wall or ceiling of an at least partially enclosed space such as a room, an auditorium, a concert hall, a religious venue (eg. a church, a synagogue, a mosque), a sports arena and a stadium. More particularly, the unit 102 is installed near the acoustic reflective surface 106 to dampen sound travelling toward the reflective surface 106 before the sound reflects from the reflective surface 106 to become an echo or contribute to reverberation. Thus, the invention attempts to remove reflections at, or very near, the point of reflection without deleteriously affecting the sound in the bulk of the space.

Accordingly, input microphone 110 detects an incident audio wavefront 108 travelling towards the reflective surface 106 and feeds an electronic signal representative of the incident audio wavefront 108 to the control module 116. The control module calculates a cancelling audio wave 118 that is substantially of the same amplitude but opposite in polarity (i.e., equal amplitude, opposite phase) to the incident audio wavefront 108. The control module 116 plays the cancelling audio wave 118 through the loudspeaker 112. The loudspeaker 112 is preferably a highly directional audio source as known in the art per se that faces the reflective surface 106 so as to highly attenuate the incident audio wavefront 108 at or near the reflective surface 106 without excessive bleeding of the cancelling audio wave 118 back towards the audio source 104 or the audience. The error microphone 114 is used to sample the sound substantially at the reflective surface 106 and provide a feedback signal to the control module 116.

The control module 116 executes a noise cancellation algorithm that preferably outputs the cancelling audio wave signal within a set delay time T (between the time the input microphone senses the incident wave and the loudspeaker plays the cancellation wave). With this knowledge, the input microphone 110 is preferably spaced a distance D away from the loudspeaker 112 corresponding to time T required for the incident audio wavefront 108 to travel between these components. Depending on the noise cancellation algorithm employed, the delay time T may also be adaptively tuned based on the feedback provided by the error microphone 114. (The delay time may be adjusted in the algorithm that adaptively computes the weights of digital filter taps, as such algorithms are discussed in greater detail below.)

The sound dampening unit 102 may be assembled onto a rigid frame bolted onto the reflective surface 106. Alternatively, the components of the unit may be independently mounted in the at least partially enclosed space. For example, the components may be suspended from the ceiling.

Figure 2:
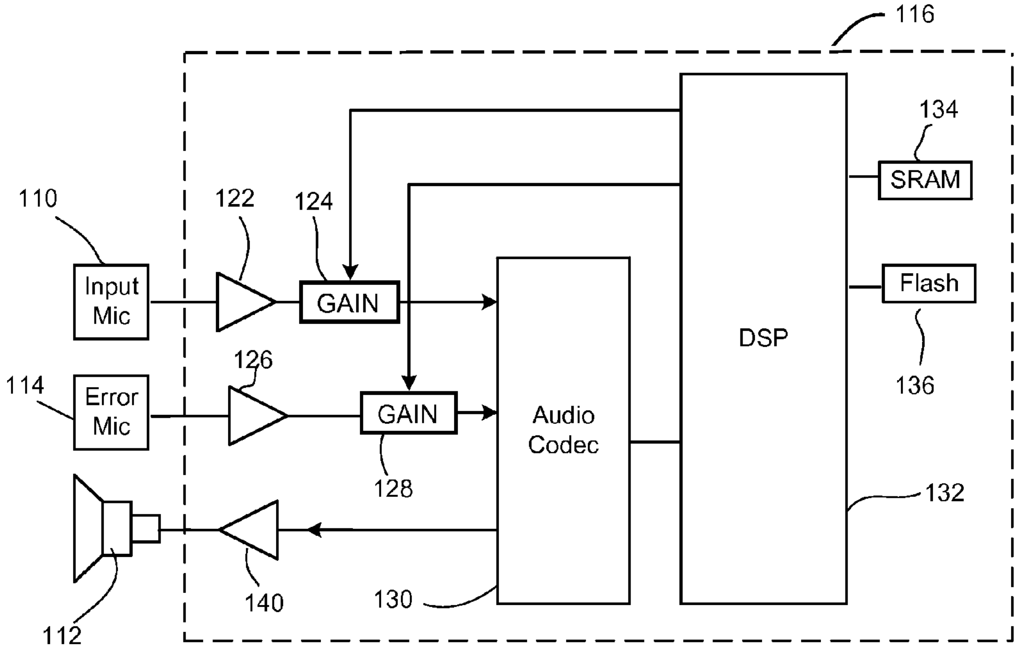
FIG. 2 is an electronic system block diagram of a control module employed in the system shown in FIG. 1.

FIG. 2 is a system block diagram of an exemplary version of the control module 116. The input microphone 110 is connected to a preamplifier 122 which optionally feeds into a first gain stage 124 for maintaining overall system dynamic range. The error microphone 114 is likewise connected to a preamplifier 126 which feeds into a second gain stage 128. The input and error microphone signals are then applied to an audio coder/decoder ('codec') 130 for converting the analog microphone signals into digital input and error audio signals. The audio codec 130 is connected via a high speed connection to a digital signal processor (DSP) 132. An example of suitable integrated circuits for the DSP and codec is the TMS320C6472 DSP and TLV320AIC3254 codec from Texas Instruments. A high speed random access memory 134 for computational purposes and a flash memory 136 for storing boot programming and other purposes may be connected to the DSP 132. The DSP 132 executes the sound cancellation algorithm and provides the cancelling audio wave signal to the audio codec 130 which feeds a power amplifier 140 that drives the loudspeaker 112.

Figure 3:
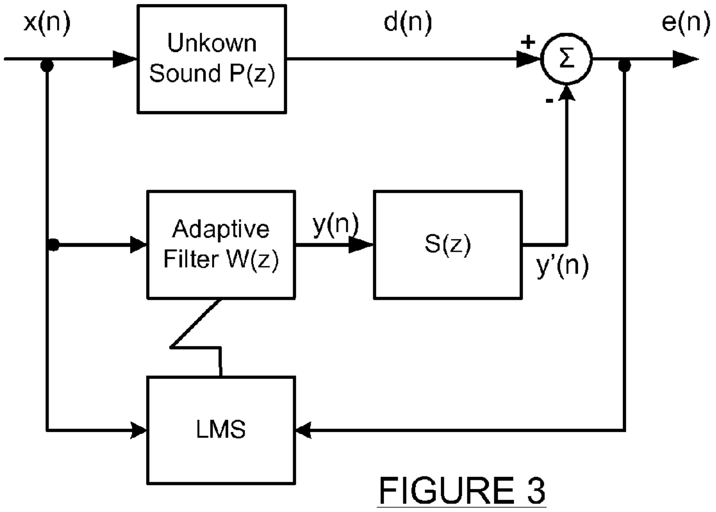
FIG. 3 is a logical block diagram of a controller employed by the system shown in FIG. 1.

From a control point-of-view, the sound dampening unit 102 may be implemented as a single channel broadband adaptive feedforward control system having a single reference sensor, a single secondary source and a single error sensor. A suitable control system which takes into account secondary path effects S(z) resulting from the electronic circuitry and the acoustic path from loudspeaker to the error microphone where the incident wavefront is combined with the output of loudspeaker is shown in FIG. 3. In this model, x(n) is the incident audio wavefront 108 as sampled by the input microphone 110. The summing junction represents the superposition of the cancelling audio wave 118 (FIG. 1) from loudspeaker 112 with the incident audio wavefront 108, with e(n) (FIG. 3) representing the error in the superpositioned sound. W(z) is an adaptive filter implemented by the DSP 132 that is used to estimate an unknown space P(z) representing the primary acoustic path from the input microphone 110 to the error microphone 114, and y(n) is the output of the adaptive filter. S(z) is the secondary path transfer function. The aim of the adaptive filter is to minimize the power of the error signal e(n), and a least mean square (LMS) block implemented by the DSP 132 adaptively modifies the weights of W(z).

If desired, the feedback caused by the cancelling audio wave 118 being picked up the input microphone 110 may also be neutralized by the use of a separate feedback cancellation filter. See generally, Kuo and Morgan, "Active Noise Control: A Tutorial Review", Proceedings of the IEEE, Vol. 87, No. 6, June 1999, the contents of which are incorporated herein by reference in their entirety.

An alternative noise cancellation algorithm that may provide a more stable system includes the filtered-X LMS algorithm (Widrow and Stearns, 1985). Faster converging algorithms include the recursive least square algorithm (Kuo and Morgan, 1996), and neural network based techniques.

Figure 4:
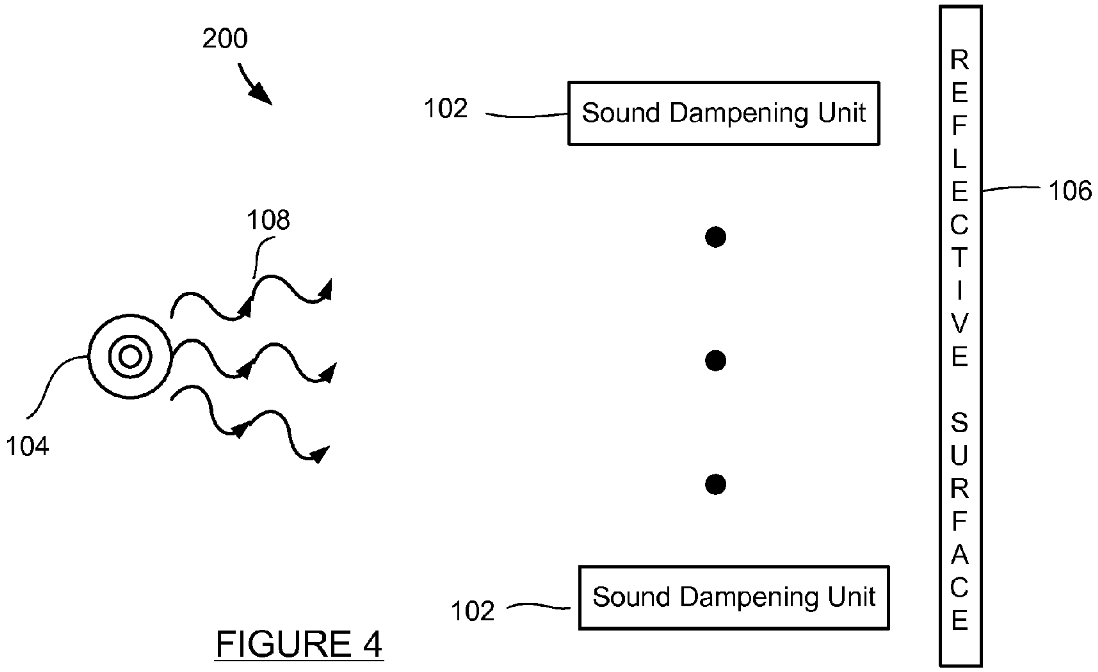
FIG. 4 is a schematic diagram of a reverberation control system according to a second embodiment.

FIG. 4 shows a variant 200 of the reverberation control system shown in FIG. 1. In the reverberation control system 200, multiple sound dampening units 102 are deployed along and proximate to the reflective surface 106, such as a wall or ceiling. Each unit 102, however, is a single channel system, functioning essentially independently of every other unit 102.

Figure 5:
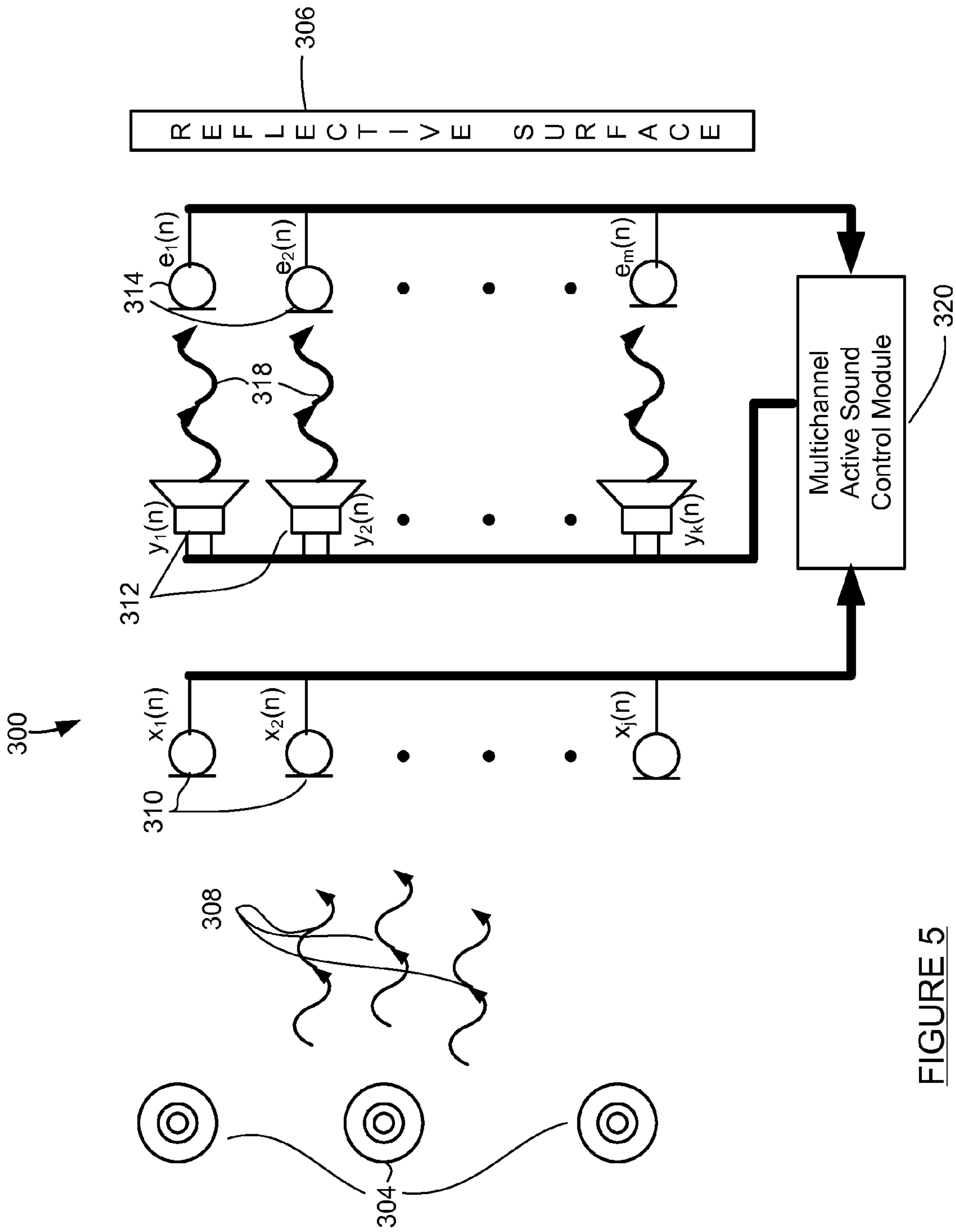
FIG. 5 is a schematic diagram of a reverberation control system according to a third embodiment.

FIG. 5 shows another more preferred embodiment of a reverberation control system 300 that employs a multiple-channel active sound control module that interlinks several input microphones 310, several cancelling loudspeakers 312 and several error microphones 314 proximate a reflective surface 306. This system can be deployed in larger auditoriums, venues or halls where there may be several audio sources 304 broadcasting sound, resulting in a more complex incident wavefront 308.

The illustrated multi-channel reverberation control system 300 employs J input microphones 310 to form a reference signal vector. The system generates K cancelling signals to drive the cancelling loudspeakers 312, and utilizes M error microphones 314 distributed along the area of the reflective surface(s) to measure the residual sound.

Figure 6:
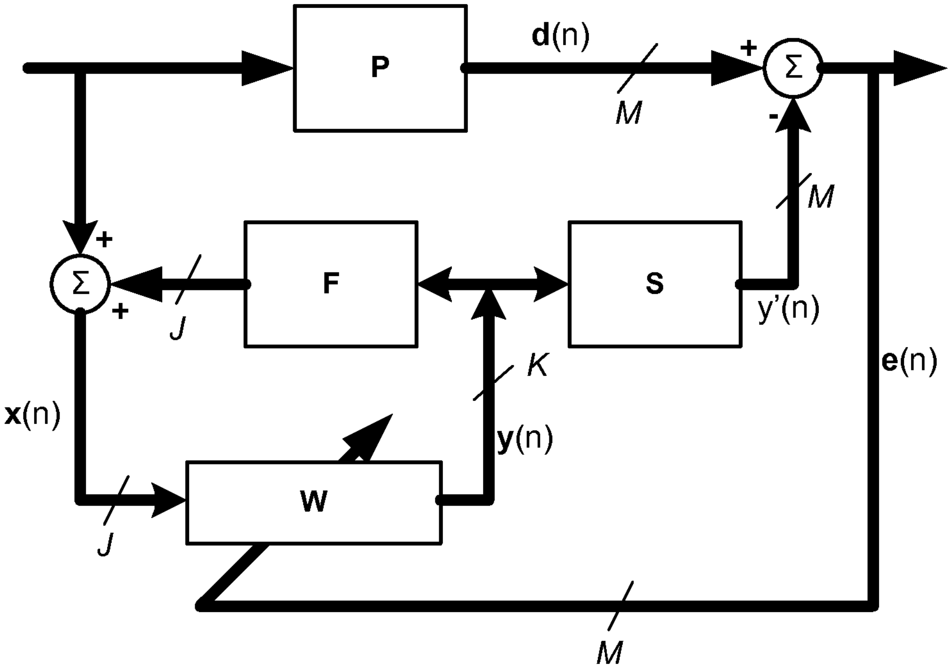
FIG. 6 is a logical block diagram of a controller employed by the system shown in FIG. 5.

A logical block diagram of a suitable controller 320 is shown in FIG. 6. The wide arrows represent an array of electrical or acoustic signals that are symbolically expressed as vectors. The matrix P represents M×J primary path transfer functions, $P_{mj}(z)$, from the audio source to each error microphone output, $E_m(n)$. The matrix S represents M×K secondary-path transfer functions, $S_{mk}(z)$, from the K cancelling loudspeakers 312 to the M error microphones 314. The controller 320 also incorporates feedback paths from the cancelling loudspeakers 312 to the input microphones and matrix F represents J×K feedback paths, $F_{jk}(z)$, from the K cancelling loudspeakers 312 to the J input microphones 310. There are thus K×J possible feedforward channels, each having a separate adaptive filter, the K×J adaptive filters $W_{k,j}(z)$ being represented by the matrix W. A multiple-reference/multiple-output filtered-X LMS algorithm is employed for adaptively determining the weights of the filter taps.

Alternative controllers include those that employ subband techniques where the adaptive weights are computed in subbands but are then collectively transformed into an equivalent set of wideband filter coefficients. Processing the signals in subbands can reduce the computational load and result in faster convergence of filter weights because the frequency range is reduced in each subband. See Morgan and Thi, "A delayless subband adaptive filter", IEEE Trans. Signal processing, vol. ASSP-32, pp. 304-337, April 1984.

As will be seen, the reverberation control systems 100, 200, 300 are deployed to attenuate sound at or near a reflection surface in order to prevent or at least reduce the sound from reverberating back into a listening area. The invention thus differs from the prior art that attempted to create a 'quiet zone' by attenuating directly incident sounds plus reverberations from the sounds that do reflect into the listening area. In the 'quiet zone' application, the digital filter may require a large number of taps in order to deal with the reverberations. This increases the computational load on the DSP, necessitating either a more powerful DSP processor or limiting the type of noise cancellation algorithms to those having relatively low computational requirements, such as delayless subband adaptive filters. However, the applications discussed herein that attempt to stop or limit reverberations before they become a problem for the listener will likely result in a digital filter requiring a comparatively smaller number of taps.

From the foregoing it will be appreciated that the reverberation control system can be applied in a variety of environments. A concert hall is one environment. Churches with high ceilings that tend to have many reflective surfaces are another environment. Other environments include bus and train stations where reverberations can make announcements unintelligible. The invention can also be applied in factory environments to reduce machine noise reflected from the ceilings or walls around a noisy machine to reduce the overall noise in the factory.

Another advantage of providing the reverberation control system relates to the environment outside the venue in which the system is installed. Without a reverberation control system such as that which has been described herein, some sound energy is transmitted through the structure of the venue itself and out into the surrounding environment (eg. the surrounding neighbourhood), which may be undesirable to people in that surrounding environment. Because the reverberation control system reduces the amount of sound energy that reaches the structure of the venue, the amount of sound that is transmitted out of the venue is reduced, and as a result, surrounding buildings, houses and the like are not subjected to as much noise. Furthermore, the structure of the venue itself may incur a reduced amount of sound wave-initiated damage (eg. cracks in an interior façade due to fatigue resulting from the impact of sound waves thereon) as a result of the reduced amount of sound energy that reaches the structure.

Figure 7:
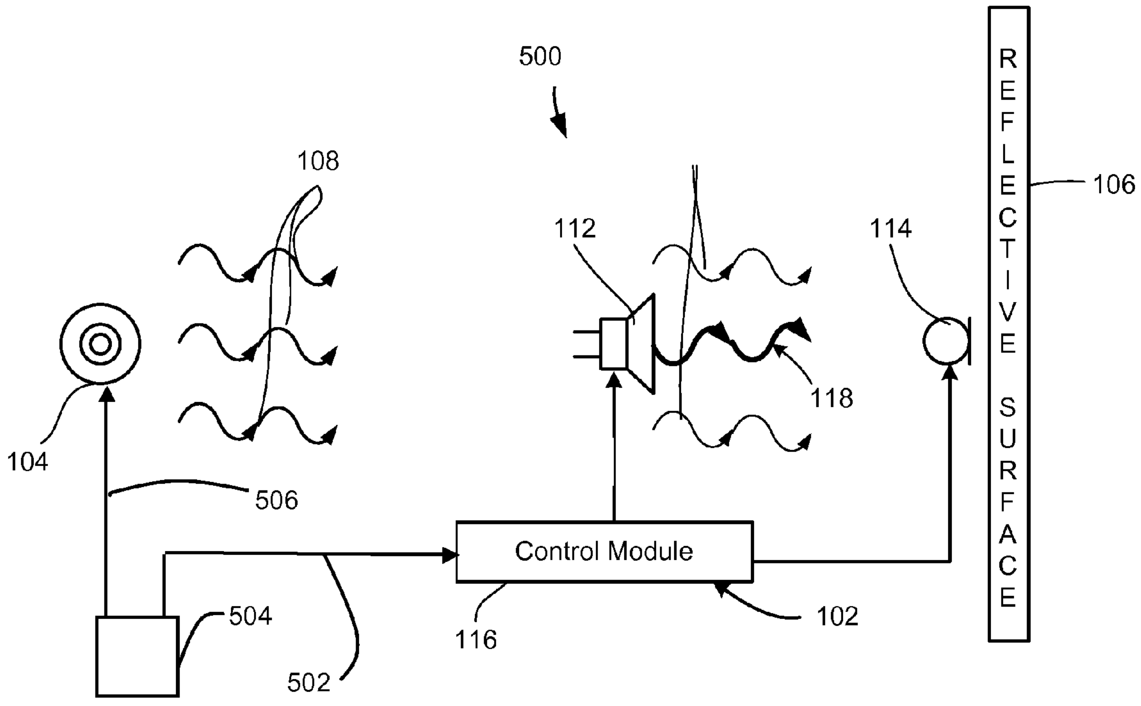
FIG. 7 is a schematic diagram of a reverberation control system according to a fourth embodiment.

In another embodiment shown at 500 in FIG. 7, the same reference numerals as shown in FIG. 1 are used to indicate analogous components. A primary difference between the embodiment in FIG. 7 and the embodiment shown in FIG. 1 is that in the embodiment in FIG. 7, the control module 116 receives audio signals via conduit 502 from audio signal source 504, which is the audio signal source that feeds the audio source 104 through conduit 506, instead of receiving signals from an input microphone. The control module 116 processes the audio signal from conduit 502 to generate a cancelling audio wave 118 via loudspeaker 112 that at least in part cancels the incident audio wave 108. The incident audio wave 108 is made up largely of the source audio (ie. the audio that is emitted from the speaker 104), but may also include other audio such as, for example, audience noise, ventilation noise and audio reflected from other surfaces of the venue. The system 500 uses the error microphone 114 similarly to the embodiment shown in FIG. 1 (ie. to sample the sound substantially at the reflective surface 106 and provide a feedback signal to the control module 116).

While the above describes particular embodiments of the invention, it will be appreciated that modifications and variations may be made to the detailed embodiment described herein without departing from the spirit of the invention.

The invention claimed is:

1. A method of increasing the intelligibility of an audio broadcast in an at least partially enclosed space from at least one audio source, the method comprising:

receiving an incident audio wavefront travelling towards a reflective surface from the audio source at a first position in the at least partially enclosed space;

generating a cancelling audio wavefront having a magnitude substantially equal to the magnitude of incident audio wavefront and a phase substantially opposite to the phase of the incident audio wavefront; and broadcasting the cancelling audio wavefront at a second position in the at least partially enclosed space, the second position being adjacent to the reflective surface of the at least partially enclosed space and downstream of the first position relative to the audio source, the cancelling audio wavefront being broadcast toward the reflective surface, thereby to attenuate the incident audio wavefront substantially at or near the reflective surface in order to reduce reverberations of the incident audio wavefront.

2. A method according to claim 1, wherein the incident audio wavefront is received via at least one input microphone.

3. A method according to claim 2, wherein the cancelling audio wavefront is broadcast through at least one directional loudspeaker positioned adjacent to, and facing, the reflective surface.

4. A method according to claim 3, wherein the cancelling loudspeaker is spaced at a distance D away from the input microphone, D corresponding to a time required to generate the cancelling audio wavefront.

5. A method according to claim 4, wherein an array of input microphones and corresponding cancelling loudspeakers are deployed across the breadth of the reflective surface.

6. A method according to claim 1, wherein the cancelling loudspeaker is spaced at a distance D away from the input microphone, wherein D is selected to provide sufficient time to generate and broadcast the cancelling audio wavefront timed to attenuate the incident audio wavefront.

7. A method of increasing the intelligibility of an audio broadcast in an at least partially enclosed space from at least one audio source, the method comprising:

deploying at least one input microphone in the at least partially enclosed space to convert at least one incident audio wavefront travelling towards a reflective surface into at least one corresponding reference electrical signal;

deploying at least one cancelling loudspeaker adjacent the reflective surface in the at least partially enclosed space to broadcast at least one secondary audio wavefront toward the reflective surface;

deploying at least one error microphone substantially at the reflective surface to convert a superposition of the at least one incident audio wavefront and the at least one secondary audio wavefront into at least one error electrical signal;

generating at least one cancellation signal based on the at least one reference electrical signal so as to minimize the power of the at least one error electrical signal; and converting the cancellation signal into said at least one second audio wavefront.

8. A method according to claim 7, wherein each cancelling loudspeaker is positioned adjacent to the reflective surface and has a highly directional output directed downstream in relation to the incident audio wavefront.

9. A method according to claim 8, wherein each cancelling loudspeaker is spaced at least a distance D away from a corresponding input microphone, where D corresponds to a time required to generate the cancelling audio wavefront.

10. A method according to claim 8, wherein an array of input microphones, an array of cancelling loudspeakers, and an array of error microphones are deployed across the breadth of the reflective surface.

11. A method according to claim 10, wherein the number of input microphones, cancelling loudspeakers and error microphones are equal.

12. A method according to claim 11 wherein, each input microphone, cancelling speaker and error microphone triplet form an independent, single-channel, sound dampening unit, and a plurality of single channel sound dampening units are deployed across the breadth of the reflective surface.

13. A method according to claim 10, wherein the input microphones, cancelling loudspeakers and error microphones are interlinked via a multiple-channel active sound control module.

14. A method according to claim 7, wherein the cancelling loudspeaker is spaced at a distance D away from the input microphone, wherein D is selected to provide sufficient time to generate and broadcast the cancelling audio wavefront timed to attenuate the incident audio wavefront.

15. A method of broadcasting audio with reduced reverberation in an at least partially enclosed space, the method comprising:

broadcasting an incident audio wave from at least one audio source towards a reflective surface;

transmitting a signal that is representative of the audio to a control module;

generating, using the control module, a cancelling audio wave having a magnitude substantially equal to the magnitude of incident audio wave and a phase substantially opposite to the phase of the incident audio wave; and broadcasting the cancelling audio wave toward the reflective surface from a position adjacent to the reflective surface of the at least partially enclosed space and downstream in relation to the incident audio wave broadcasted from the at least one audio source, thereby attenuating the incident audio wave substantially at or near the reflective surface in order to reduce reverberations of the incident audio wave.

* * * * *